(12) United States Patent
Hwang et al.

(10) Patent No.: US 9,511,048 B2
(45) Date of Patent: Dec. 6, 2016

(54) USE OF FLAVONE COMPOUND FOR PREVENTION OR TREATMENT OF OBESITY

(71) Applicant: INDUSTRY-ACADEMIC COOPERATION FOUNDATION, YONSEI UNIVERSITY, Seoul (KR)

(72) Inventors: Jae-Kwan Hwang, Goyang-si (KR); Myung Suk Kim, Seoul (KR); Ga Hui Oh, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/541,389

(22) Filed: Mar. 4, 2015

(65) Prior Publication Data

US 2015/0209324 A1 Jul. 30, 2015

Related U.S. Application Data

(63) Continuation of application No. PCT/KR2013/004375, filed on May 16, 2013.

(30) Foreign Application Priority Data

May 16, 2012 (KR) ........................ 10-2012-0051779

(51) Int. Cl.
*A61K 31/353* (2006.01)
*A61K 31/352* (2006.01)

(52) U.S. Cl.
CPC ............ *A61K 31/353* (2013.01); *A23K 20/111* (2016.05); *A23K 20/121* (2016.05); *A23L 33/105* (2016.08); *A23L 33/30* (2016.08); *A61K 31/352* (2013.01)

(58) Field of Classification Search
None
See application file for complete search history.

(56) References Cited

FOREIGN PATENT DOCUMENTS

KR 10-2008-0113326 12/2008

OTHER PUBLICATIONS

Azuma, Toshiaki. Antimutagenic and α-glucosidase inhibitory effects of constituents from Kaempferia parviflora. Food Chemistry. 125 (2011) 471-475.*
Hollander, et al., Acarbose in the Treatment of Type I Diabetes, Diabetes Care, Mar. 1997, vol. 20, Issue 3, pp. 248-253.
Hollander, Anti-Diabetes and Anti-Obesity Medications: Effects on Weight in People With Diabetes, Diabetes Spectrum, vol. 20, Issue 3, pp. 159-165.
Azuma, et al., "Antimutagenic and a-glucosidase inhibitory effects of constituents from Kaempferia parviflora", Elsevier, 2011, vol. 55, pp. 471-475.
Panthong, et al., "Anti-Inflammatory Activity of 5, 7-Dimethoxyflavone", Planta Medica, 1989, pp. 133-136.
Bjorn Richelsen, "Prostaglandin E 2 Action and Binding in Human Adipocytes: Effects of Sex, Age, and Obesity, Metabolism", 1988, pp. 268-275, vol. 37 No. 3.
Akase et al., "Antiobesity effects of Kaempferia parviflora in spontaneously obese type II diabetic mice", Journal of Natural Medicine, 2011, vol. 65, pp. 73-80.
Tsuji, et al., "Accumulation and metabolism of the anticancer flaconoid 5, 7-dimethoxyflavone compared to its unmethylated analog chrysin in the Atlantic killifish", Chemico-Biological interactions, 2006, vol. 164, pp. 85-92.
Peter G. Kopelman, "Obesity as a medical problem", Nature, Apr. 6, 2000, pp. 635-643, vol. 404.
Ng, et al., "The prevalence and trends of overweight, obesity and nutrition-related non-communicable diseases in the Arabian Gulf States", obesity reviews, international assoc. for the study of obesity, 2010 vol. 12, pp. 1-13.
Lai, et al., "Xanthigen Suppresses Preadipocyte Differentiation and Adipogenesis through Down-regulation of PPAR and C/EBPs and Modulation of SIRT-1, AMPK, and FoxO Pathways", Journal of Agricultural and Food Chemistry, 2012, pp. 1094-1101.
Sohle, et al., "White Tea extract induces lipolytic activity and inhibits adipogenesis in human subcutaneous (pre)-adipocytes", Nutrition & Metabolism, 2009, vol. 6:20, pp. 1-10.
Duncan, "Peroxisome Proliferator Activated Receptor-Alpha (PPARa) and PPAR Gamma Coactivator-1alpha (PGC-1a) Regulation of Cardiac Metabolism in Diabetes", NIH Public Access, Mar. 2011, pp. 1-10.
Jong Won Yun, "Possible anti-obesity therapeutics from nature—A review", Elsevier, 2010, Phytochemistry 71, pp. 1625-1641.
Sae-Wong, et al., "Anti-inflammatory mechansm of Kaempferia parviflora in murine macrophage cells (RAW 264.7) and in experimental animals", Elsevier, 2009, Journal of Ethnopharmacology 124, pp. 576-580.
Mahaboob S. Khan, et al., "Methylated chrysin induces co-ordinated attenuation of the canonical Wnt and NF-kB signaling pathway and upregulates apoptotic gene expresson in the early hepatocarcinogenesis rat model", Elsevier, 2011, Chemico-Biological Interactions 193, pp. 12-21.

(Continued)

*Primary Examiner* — Samantha Shterengarts
(74) *Attorney, Agent, or Firm* — H.C. Park & Associates, PLC

(57) ABSTRACT

The present invention relates to a pharmaceutical composition containing flavone compound as an active ingredient for treating obesity, and more specifically to a pharmaceutical composition for preventing or treating obesity and a dietary composition for preventing or reducing obesity containing 5,7-dimethoxyflavone or 5,7,4'-trimethoxyflavone. The compound according to the present invention inhibits adipogenesis, and reduces expression of the key transcription factors (SREBP1c and C/EBP) related to lipogenesis and of enzyme proteins (FAS and ACC) related to adipogenesis, and thus is effective in preventing or treating obesity.

3 Claims, 3 Drawing Sheets

(56) References Cited

OTHER PUBLICATIONS

Tewtrakul, et al., "Anti-allergic activity of some selected plants in the Zingiberaceae family", Elsevier, 2007, Journal of Ethnopharmacology 109, pp. 535-538.

Young-Gyu Kang, et al., "5,7-Dimethoxyflavone induces melanogenesis in B16F10 melanoma cells through cAMP-dependent signalling", John Wiley & Sons A/S, Experimental Dermatology, 2011, vol. 20, pp. 445-456.

Shen et al., "Pentamethylquercetin generates beneficial effects in monosodium glutamate-induced obese mice and C2C12 myotubes by activating AMP-activated protein kinase", Diabetologia (2012) 55:1836-1846, Mar. 14, 2012, Springer-Verlag 2012.

Matsuda, et al., "Structural requirements of flavonoids for the adipogenesis of 3T3-L1 cells", Bioorganic & Medicinal Chemistry 19 (2011) 2835-2841, Apr. 13, 2011, Kyoto Pharmaceutical University, Yamashina-ku, Kyoto 607-8412, Japan.

Yenjai et al., "Structural Modification of 5,7-Dimethoxyflavone from Kaempferia parvifiora and Biological Activities", Archives of Pharmacal Research, vol. 32, No. 9, 1179-1184, Aug. 4, 2009, Springer.

Extended European Search Report dated Dec. 14, 2015 in European Application No. EP13791509.6.

* cited by examiner

USE OF FLAVONE COMPOUND FOR PREVENTION OR TREATMENT OF OBESITY

TECHNICAL FIELD

This application claims priority to Korean Patent Application No. 10-2012-0051776 filed on May 16, 2012, which is hereby incorporated by reference herein in its entirety.

The present invention relates to the use of flavone compounds for preventing or treating obesity, and more specifically relates to a pharmaceutical composition for preventing or treating obesity and a dietary composition for preventing or reducing obesity containing 5,7-dimethoxyflavone or 5,7,4'-trimethoxyflavone.

BACKGROUND ART

Obesity is a medical condition of abnormal fat accumulation caused by the imbalance between energy intake and expenditure. Obesity is considered as a serious public health problem worldwide. The prevalence of obesity is increasing noticeably in Korea as well owing to various factors such as rapid industrial growth, westernization of dietary patterns, and insufficient physical activity. In addition to its own risk, obesity increases the likelihood of hyperinsulinemia, arteriosclerosis, cardiovascular diseases, certain types of cancer, and diabetes, making it more serious (Nature, 404(6778): 635-643, 2000, Obes. Rev. 12(1): 1-13, 2011).

Adipose tissue is an energy-storing organ. Excessive energy intake is a direct cause of obesity because it accelerates adipocyte differentiation and increases fat storage in the human body.

Adipocyte differentiation refers to the process in which preadipocytes proliferate and differentiate into mature adipocytes. During this process, lipogenesis-related proteins FAS (fatty acid synthase) and ACC (acetyl-CoA carboxylase) are expressed under the control of transcription factors such as PPARγ (peroxisome proliferator-activated receptor gamma), C/EBPs (CCAAT/enhancer binding proteins), and SREBP1c (sterol regulatory element binding protein 1c). These transcription factors are induced at different time points during the process, and interact with each other to regulate adipocyte-specific gene expression and to induce adipocyte differentiation (J. Agri. Food Chem. 60(4): 1094-1101, 2012, Nutr. Metab. 6(20): 1-20 2009).

Differentiated adipocytes store triglycerides in the cytoplasm. AMPK (AMP-activated protein kinase) activation stimulates signaling pathways which increase energy production involving glucose transport and fatty acid oxidation. Subsequently generated energy is consumed during physical exercise and thermogenesis. Thermogenesis is mediated by UCPs (uncoupling proteins) present in the mitochondrial inner membrane in adipose tissues and muscles, regulating energy homeostasis in the body. Expression of UCPs is known to be regulated by transcription factors PPAR and PGC-1 (peroxisome proliferator-activated receptor coactivator-1) (Pediatr. Cardiol. 32(3): 323-328, 2011).

Among the representative anti-obesity drugs developed so far, Reductil™ (Abbott, USA), which suppresses the appetite, and Xenical™ (Roche, Swiss), which blocks fat absorption, are currently used clinically for the treatment of obesity. However, therapeutic effects of these drugs are not sufficiently sustainable because of side-effects associated with cardiovascular and respiratory conditions, hypertension, and insomnia (Phytochem. 71: 1625-1641, 2010). Therefore, research is actively underway to develop anti-obesity drug substance from natural sources having a good safety profile with less adverse side-effects such as plant extracts rather than synthetic chemicals.

DISCLOSURE

Technical Problem

The present inventors discovered flavone compounds which can suppress lipid production while looking for natural materials with anti-obesity activity, thereby completing the present invention. Flavones, a class of flavonoids originated from natural materials, are reported to be effective in functions such as anti-inflammation (J. Ethnopharmacol. 124(3): 576-580, 2009), anti-cancer (Chem. Biol. Interact. 193(1): 12-21, 2011), anti-allergy (J. Ethnopharmacol. 109 (3): 53-58, 2007), and melanogenesis (Exp. Dermatol. 20(5): 445-447, 2011). However it is not known whether flavones have any effect on obesity.

Therefore, the objective of the present invention is to provide a pharmaceutical composition for preventing or treating obesity comprising a compound represented by the following Formula 1 or salt thereof as an active ingredient.

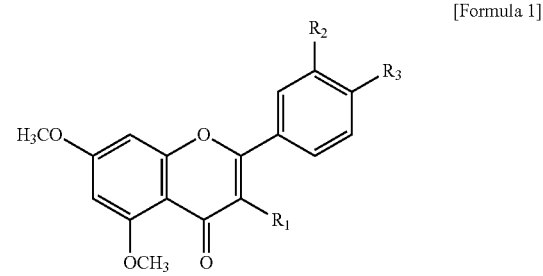

[Formula 1]

In Formula 1, each of R1, R2, and R3 independently denotes a hydrogen or a methoxy group.

Another object of the present invention is to provide a dietary composition for preventing or reducing obesity comprising a compound represented by Formula 1 or salt thereof as an active ingredient.

Technical Solution

To achieve the above object, the present invention provides a pharmaceutical composition for preventing or treating obesity comprising a compound represented by Formula 1 or salt thereof as an active ingredient.

To achieve another object, the present invention provides a dietary composition for preventing or reducing obesity comprising a compound represented by Formula 1 or salt thereof.

Hereafter, the present invention is described in detail.

The present invention provides a pharmaceutical composition for preventing or treating obesity comprising a compound represented by Formula 1 or salt thereof as an active ingredient.

Also, the present invention provides a dietary composition for preventing or reducing obesity comprising a compound represented by Formula 1 or salt thereof as an active ingredient.

Preferably a compound of Formula 1 may be 5,7-dimethoxyflavone or 5,7,4'-trimethoxyflavone.

5,7-dimethoxyflavone or 5,7,4'-trimethoxyflavone of the composition of the present invention may be produced by chemical synthesis or isolated and purified from *Kaempferia parviflora* or other plants.

The compound of the present invention inhibits lipid production by preventing differentiation of 3T3-L1 preadiocytes, and reduces expression levels of key transcription factors involved in lipogenesis (SREBP1c and C/EBP) and lipogenic enzymes (FAS and ACC) (refer to Example 1 and Example 2). Furthermore, the compound of the present invention reduces body weight of obese mice effectively (refer to Example 3).

The flavone compound of the present invention may be used as it is, as a salt thereof, or in the form of a pharmaceutically acceptable salt. As used herein, the phrase "pharmaceutically acceptable" means that the components present in the composition are physiologically acceptable and usually do not invoke allergic or similar reactions when administered to humans. Preferably, the salt may be an acid addition salt formed from a pharmaceutically acceptable free acid. The free acid may be an organic or inorganic acid. The organic acid includes but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. Also, the inorganic acid includes but is not limited to hydrochloric acid, bromic acid, sulfuric acid and phosphoric acid.

The pharmaceutical composition according to the present invention may comprise a compound represented by Formula 1 or salt thereof alone or in combination with one or more appropriate carrier, excipient or diluent generally used in the preparation of pharmaceutical compositions.

A pharmaceutically effective amount of the flavone compound according to the present invention may be 0.001 to 300 mg/day/kg body weight, and preferably 0.01 to 200 mg/day/kg body weight. However, a pharmaceutically effective amount may be suitably determined by considering various factors such as types of diseases, disease severity, patient's age, body weight, health condition, sex, administration routes and treatment length.

As used herein, "pharmaceutically acceptable" means non-toxic composition which is physiologically acceptable and, when administered to human beings, generally does not cause allergic reactions, such as gastrointestinal disorder and dizziness, or similar reactions thereto as well as not inhibiting reaction of an active ingredient. The carrier comprises all kinds of solvents, dispersing media, oil-in-water or water-in-oil emulsions, water soluble compositions, liposomes, microbeads and microsomes.

Meanwhile, the pharmaceutical composition of the present invention may be formulated with a proper carrier according to the routes of administration. Administration routes of the pharmaceutical composition according to the present invention may be, but not limited thereto, oral or parenteral. For example, parenteral administration may include various routes such as transdermal, intranasal, intraperitoneal, intramuscular, subcutaneous or intravenous administration.

In case of oral administration, the composition of the present invention may be formulated with a proper carrier for oral administration into powders, granules, tablets, pills, and sugar-coated tablets, capsules, liquids, gels, syrups, slurries, and emulsions by using the methods well-known in the art. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. Also, if desired, it may comprise cross-linked polyvinylpyrrolidone, agar, alginic acid or sodium alginate as a disintegrating agent. Further, the inventive pharmaceutical composition may comprise anticoagulants, lubricants, wetting agents, flavors, emulsifying agents and antiseptics.

Also, in case of parenteral administration, a pharmaceutical composition of the present invention may be formulated with a proper carrier for parenteral administration into injections, transdermal preparations, and nasal inhalers by using the methods well-known in the art. The injection must be sterilized and protected from microorganisms such as bacteria and fungi. Proper carriers for injection may be, but not limited to, water, ethanol, polyol (e.g. glycerol, propylene glycol and liquid polyethylene glycol) or mixture thereof and/or solvent or dispersing media comprising plant oil. More preferably, proper carriers may be Hank's solution, Ringer's solution, PBS (Phosphate buffered saline) containing triethanol amine, or a isotonic solution such as distilled water for injection, 10% ethanol, 40% ethanol, 40% propylene glycol and 5% dextrose.

To protect the injection from contamination of microorganisms, it may further comprise various antibiotics or antifungal reagent such as paraben, chlorobutanol, phenol, sorbic acid, thimerosal. In addition, in most cases, the injection may further comprise an isotonic reagent such as sugars or sodium chloride.

In case of transdermal preparations, it may comprise ointments, creams, lotions, gels, topical solutions, plasters, liniments and aerosols. The "transdermal preparations" means administering a pharmaceutical composition partially to skin and delivering an effective amount of an active ingredient through the skin. The formulation of the above-mentioned is well-described in Remington's Pharmaceutical Science, 15th Edition, 1975, Mack Publishing Company, Easton, Pa.

In case of nasal inhalers, the compound of the present invention may be delivered in a form of aerosol spray from a pressure pack or spray by using proper propellants such as dichlorofluoromethane, trichlorofluoromethane, dichlrorotetrafluoroethane, carbon dioxide or other proper gas. In case of pressure aerosols, dose may be determined by providing a valve which delivers a measured amount of the compound. For example, a gelatin capsule and cartridge for inhaler or insufflator may be formulated to contain the compound, or the powder compound of proper powder such as lactose or starch. Other pharmaceutically acceptable carriers are referenced in Remington's Pharmaceutical Sciences, 19th ed., Mack Publishing Company, Easton, Pa., 1995.

Also, a pharmaceutical composition of the present invention may further comprise one or more buffers (e.g. saline or PBS), carbohydrates (e.g. glucose, mannose, sucrose or dextran), antioxidant, bacteriostat, chelating agent (e.g. EDTA or glutathione), adjuvant (e.g. aluminium hydroxide), suspension agent, thickening agent and/or preservative.

A dietary composition of the present invention encompasses all types of food comprising functional foods, nutritional supplements, health foods, and food additives. The dietary composition may be prepared into various forms according to the methods well-known in the art.

For example, a compound represented by Formula 1 or salt thereof of the present invention itself may be prepared in the form of tea, juice or drink for drinking as a health food, or may be formulated into granules, capsules or powder. In addition, a compound represented by Formula 1 or salt thereof of the present invention may be formulated into a composition by mixing with other known substance or active ingredients with anti-obesity effect.

Additionally, a functional food may be prepared by adding a compound represented by Formula 1 or salt thereof of the present invention to beverages (including alcoholic beverages), fruits and processed foods thereof (e.g. canned fruits, bottled fruits, jam, marmalade and the like), fishes, meats, and processed foods thereof (e.g. ham, sausages, corn beef), bread and noodles (e.g. Japanese noodles, buckwheat noodles, ramen, spaghetti, macaroni and the like), juices, drinks, cookies, Korean taffy, dairy products (e.g. butter, cheese and the like), eatable plant oils, margarine, plant proteins, retort foods, frozen foods, and various seasonings (e.g. soybean paste, soy sauce, sauce and the like).

Preferably the content of a compound represented by Formula 1 or salt thereof in a dietary composition of the present invention may be, but not limited to, 0.01 to 100% (w/w) of the final food product.

Also, in order to use a compound represented by Formula 1 or salt thereof of the present invention as food additives, it may be formulated into powder or concentrate.

The present invention provides the use of a compound represented by Formula 1 or salt thereof for producing an agent to prevent or treat obesity.

The present invention provides a method for preventing or treating obesity by administering an effective amount of a compound represented by Formula 1 or salt thereof to a subject in need thereof.

A compound represented by Formula 1 or its pharmaceutically acceptable salt of the present invention may be administered by various routes including oral, transdermal, subcutaneous, intravenous or intramuscular administration with an effective amount. As used herein, "effective amount" refers to an amount of a composition or extract which exhibits the effect of preventing or treating obesity when it is administered to the patient. As used herein, "subject" may comprise an animal, particularly a mammal including humans, as well as cells, tissues, organs derived from an animal. A subject may refer to a patient in need of the treatment thereof.

The compound represented by Formula 1 or its pharmaceutically acceptable salt according to the present invention may be administered as it is or as various types of formulations prepared as described above, preferably until the treatment results in a desired effect of preventing or treating obesity. A compound or its pharmaceutically acceptable salt of the present invention may be administered by various routes according to the methods well-known in the art. Administration routes may be oral or parenteral, for example, oral, intramuscular, intravenous, intracutaneous, intraarterial, intraosseous, intrathecal, intraperitoneal, nasal, intravaginal, intrarectal, sublingual or subcutaneous administration or through the gastrointestinal tract, mucosal membrane or respiratory tract. For example, a compound or its pharmaceutically acceptable salt of the present invention may be applied topically on the skin or prepared into an injectable formulation, and then administered by lightly pricking the skin with a 30 gauge thin injection needle. Preferably it may be directly applied to the skin of a subject. In addition, a compound or its pharmaceutically acceptable salt of the present invention can be administered as attached to the molecules evoking high-affinity binding to the target cells or tissues (for example, skin cells or skin tissue), or as capsulated within such molecules. A compound or its pharmaceutically acceptable salt of the present invention can be coupled or cross-liked with sterols (for example, cholesterol), lipids (for example, cationic lipids, virosomes or liposomes) or target cell-specific bonding agents (for example, ligands recognized by target-cell specific receptors) using the methods well-known in the art. Coupling agents or cross-linking agents include, but not limited to, protein A, carbodiimide, N-succinimidyl-3-(2-pyridyldithio) propionate (SPDP).

These formulations are described in Remington's Pharmaceutical Science, 15th Edition., Mack Publishing Company, Easton, Pa., 1995, which is the general reference well known in the pharmaceutical chemistry field.

Advantageous Effect

As described above, compounds of the present invention can be useful in preventing or treating obesity by suppressing lipid production and the expression of transcription factors (SREBP1c and C/EBP) and enzymes (FAS and ACC) critically involved in lipogenesis.

MODE FOR INVENTION

Hereinafter, the present invention will be described in detail with reference to examples.

However, it is to be understood these examples are for illustrative purposes only and are not intended to limit the scope of the present invention.

Example 1

Anti-Obesity Activity of 5,7-dimethoxyflavone

<1-1> Measurements of Inhibitory Activity on Lipid Production

3T3-L1 preadipocytes (American Type Culture Collection (ATCC), Manassas, Va., USA) were cultured in DMEM (Dulbecco's Modified Eagle's Medium) supplemented with 10% bovine calf serum, and seeded into 12-well microtiter plates with a density of $10^5$ cells/well. Adipocyte differentiation was induced when the preadipocytes reached approximately 100% confluence after growing two more days at 90% confluence. For the experimental groups, induction of adipocyte differentiation was performed in the presence of 5,7-dimethoxyflavone at the concentration of 5, 10, or 20 μM dissolved in the culture medium containing dexamethasone, IBMX (3-isobutyl-1-methylxanthine), and insulin. Afterwards, cells of the experimental groups were maintained continuously in the presence of the same concentrations of 5,7-dimethoxyflavone dissolved in the culture medium containing 10% FBS and 0.1% insulin, replacing the medium every two days. For comparison, control cells were treated the same way as the cells of the experimental groups except for the 5,7-dimethoxyflavone treatment. On day 10 since induction of differentiation, fully differentiated adipocytes were stained with Oil Red O (Sigma, St. Louis, Mo., USA). Stained lipid droplets in the adipocytes were extracted with 100% isopropanol and subjected to the measurement of the absorbance at 500 nm using a spectrophotometer. Lipid accumulation in the experimental groups was compared with the controls which did not receive 5,7-dimethoxyflavone treatments, and presented as a percent (%) of the control.

Figure 1:
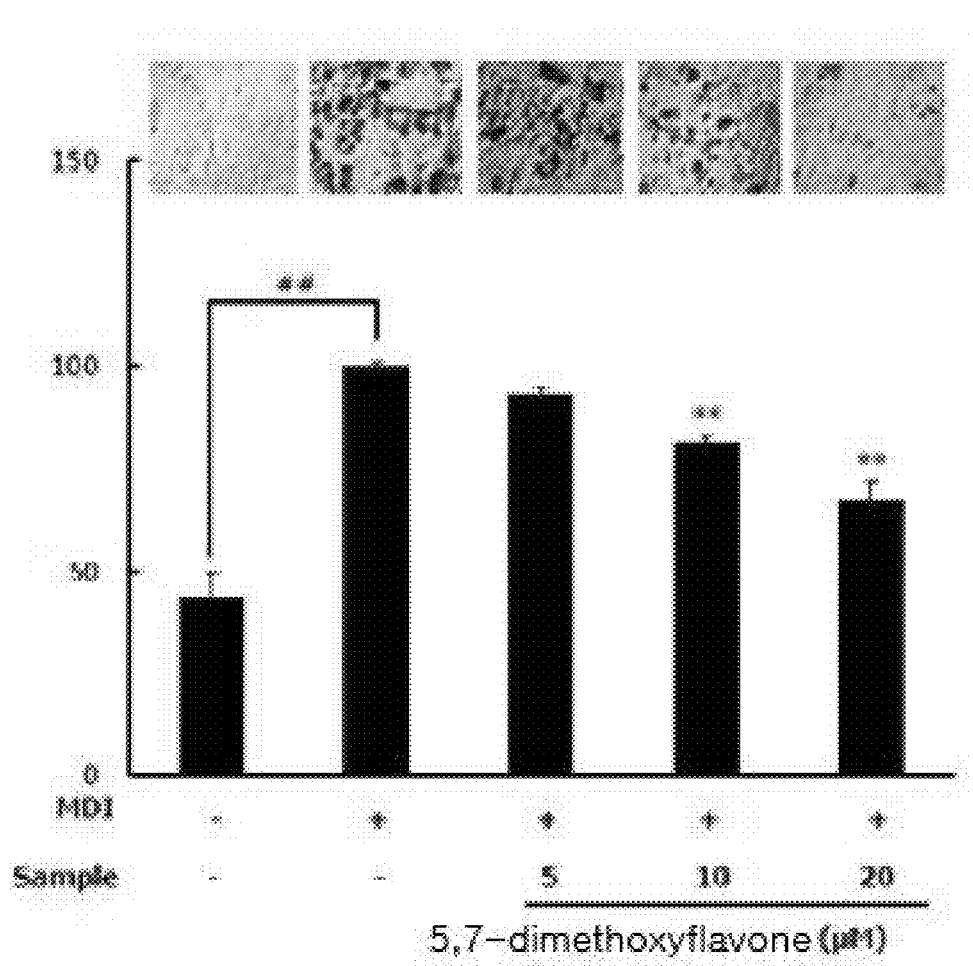
FIG. 1 shows the measurements of inhibitory activities of 5,7-dimethoxyflavone on lipogenesis in 3T3-L1 preadipocytes.

As a result, it was obvious that 5,7-dimethoxyflavone suppresses lipid production in 3T3-L1 adipocytes effectively as shown in FIG. 1.

<1-2> Effect of Reducing Expression Levels of Lipogenic Transcription Factors and Enzymes It was examined whether the expression of proteins involved in lipid production was reduced by 5,7-dimethoxyflavone treatments in 3T3-L1 adipocytes. 3T3-L1 adipocytes were induced to differentiate in the same manner as described in Example 1-1, and were lysed with a RIPA buffered solution containing a proteinase inhibitor cocktail. Protein samples were boiled for 5 minutes, loaded (20 g) on 10% SDS-PAGE gels and separated by electrophoresis. Separated proteins were transferred to the nitrocellulose membranes and subjected to western blot experiments. Protein-transferred membranes were reacted with primary antibodies, rinsed with TBST three times, 10 minutes each. The dilution ratio of primary antibodies was 1:1000. Membranes reacted with primary antibodies were followed with secondary antibody incubation (anti-rabbit horseradish) for 2 hours at room temperature. The dilution ratio of secondary antibodies was 1:5000. Protein bands were visualized with ECL western blotting detection reagents (Amersham, Tokyo, Japan). Proteins were harvested after eight days and subjected to western blot experiments.

Figure 2:
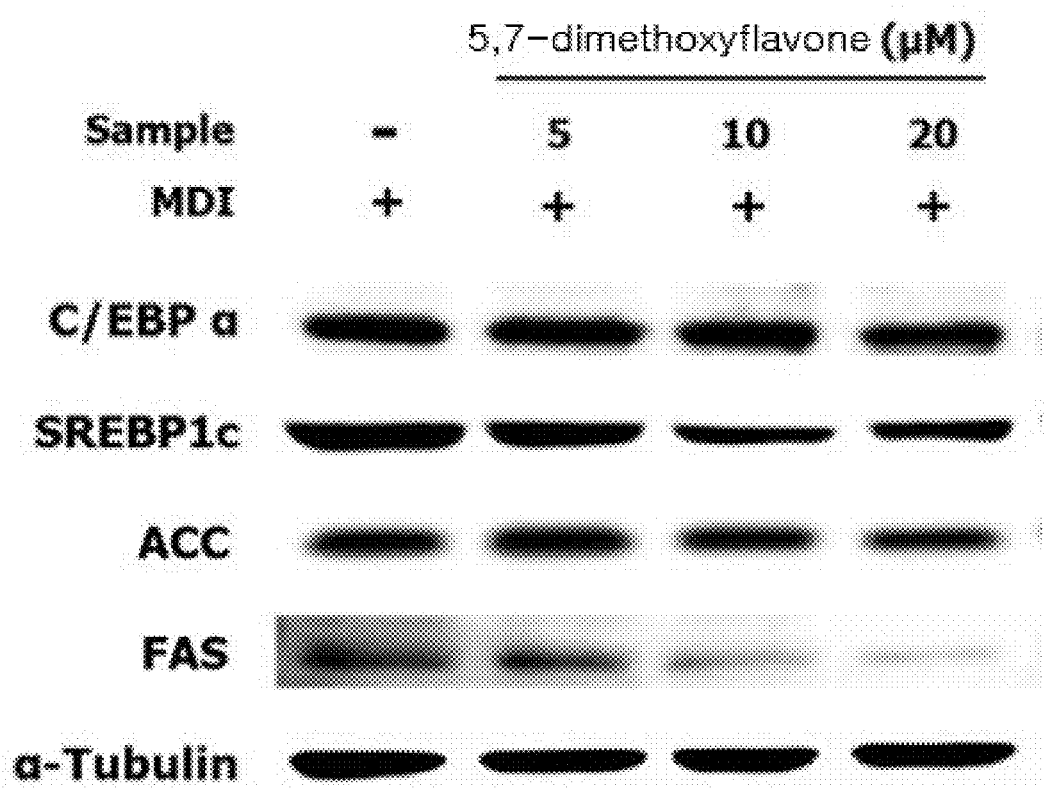
FIG. 2 shows reduction in levels of lipogenic transcription factors SREBP1c and C/EBP and lipogenic enzymes FAS an ACC induced by 5,7-dimethoxyflavone in 3T3-L1 preadipocytes.

As shown in FIG. 2, it was confirmed that 5,7-dimethoxyflavone treatments resulted in reduction in the expression of key transcription factors regulating lipid production (SREBP1c and C/EBP) and critical lipogenic enzymes (FAS and ACC). Thus, these results demonstrated a remarkable anti-obesity effect of 5,7-methoxyflavone, suppressing important signaling pathways associated with lipid production in 3T3-L1 preadipocytes.

<1-3> Effect of Increasing Expression Levels of Thermogenic Proteins

Proteins were harvested from the 3T3-L1 adipocytes differentiated as described in Example 1-1, and subjected to western blot experiments in the same manner as in Example 1-2.

Figure 3:
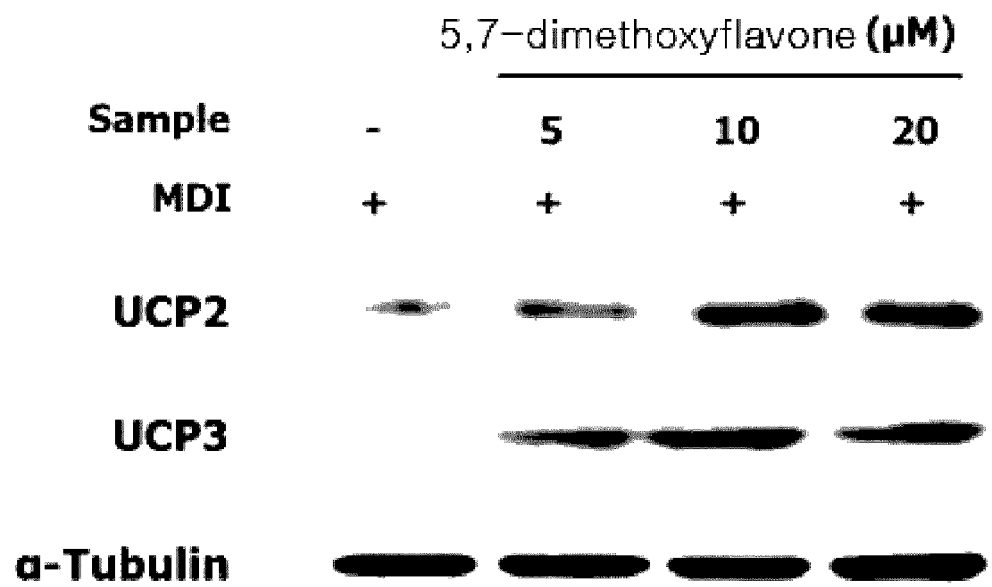
FIG. 3 shows increase in the expression levels of key thermogenic transcription factors UCP2 and UCP3 induced by 5,7-dimethoxyflavone in 3T3-L1 preadipocytes.

As shown in FIG. 3, it was found that 5,7-dimethoxyflavone treatments upregulated the expression of UCP2 and UCP3 which are vital for the process of thermogenesis, suggesting that 5,7-dimethoxyflavone exerts anti-obesity effect by accelerating fat burning.

Example 2

Suppression of Lipogenesis by 5,7,4'-trimethoxyflavone

Experiments using 5,7,4'-trimethoxyflavone at the concentration of 20 μM were performed in the same manner as in Example 1-1. The results showed a significant reduction in lipid production by 28% in the cells treated with 5,7,4'-trimethoxyflavone compared to the control (p<0.01). Taken together, results suggest that these two flavone compounds can suppress lipid production very effectively.

Example 3

Weight-Reducing Effect in the Mouse Model of Obesity

Three week-old C57BL/6 mice were acclimated for one week and fed with high-fat diet (product #D12492, Research Diet Inc., New Brunswick, N.J., USA) for six weeks to induce obesity. Mice were randomly divided into experimental and control groups, in total of four groups, ten per each group. The experimental groups were orally administered with either 5,7-dimethoxyflavone or 5,7,4'-trimethoxyflavone suspended in 0.25% carboxymethyl cellulose at a dose of 20 mg/kg body weight, once a day at regular hours for eight weeks. For comparison, the control groups were orally administered with 0.25% carboxymethyl cellulose only in the same manner as the experimental groups. Food intake and body weight of each sample mouse were measured every week. During eight weeks of treatment, measurements of food intake showed no significant difference between the experimental and control groups.

Figure 4:
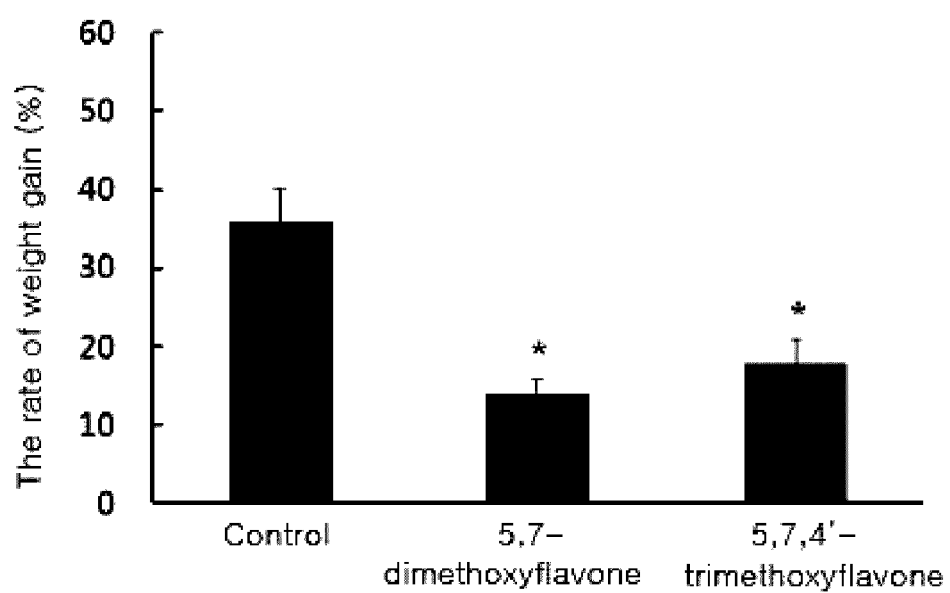
FIG. 4 shows a weight-reducing effect of 5,7-dimethoxyflavone in the mouse model of high fat diet-induced obesity.

In contrast, measurements of the rate of weight gain at the end of eight weeks was significantly lower in the experimental groups treated with either 5,7-dimethoxyflavone or 5,7,4'-trimethoxyflavone compared to the control group (p<0.05), as shown in FIG. 4. These results suggest that both 5,7-dimethoxyflavone and 5,7,4'-trimethoxyflavone are very effective in weight loss.

INDUSTRIAL APPLICABILITY

The compounds of the present invention suppress lipid production and downregulate key transcription factors (SREBP1c and C/EBP) and enzymes (FAS and ACC) involved in lipogenesis. Therefore these compounds can be used for producing a pharmaceutical composition for preventing or treating obesity, and are highly applicable in the related industry.

The invention claimed is:

1. A method for treating obesity, the method comprising administering an effective amount of a compound represented by Formula 1 or a salt thereof to a subject in need of obesity treatment

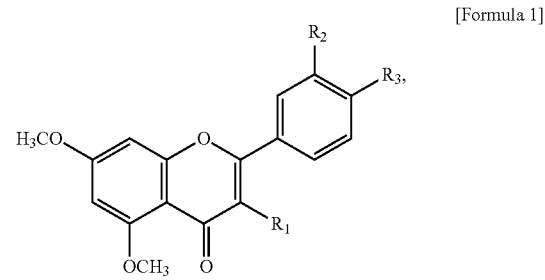

[Formula 1]

wherein each of $R_1$, $R_2$, and $R_3$ consists of hydrogen or a methoxy croup.

2. The method of claim 1, wherein the compound is 5,7-dimethoxyflavone or 5,7,4'-trimethoxyflavone.

3. The method of claim 1, wherein administering an effective amount of the compound comprises administering 0.001 to 300 mg/day/kg of body weight of the compound, or the salt thereof, to the subject in need of obesity treatment.

* * * * *